(12) United States Patent
Boettcher et al.

(10) Patent No.: US 11,592,387 B2
(45) Date of Patent: Feb. 28, 2023

(54) TEST FIXTURE AND METHOD FOR USE

(71) Applicant: The Boeing Company, Chicago, IL (US)

(72) Inventors: Philipp A. Boettcher, Charleston, SC (US); Eddie Kwon, Seattle, WA (US)

(73) Assignee: The Boeing Company, Chicago, IL (US)

( * ) Notice: Subject to any disclaimer, the term of this patent is extended or adjusted under 35 U.S.C. 154(b) by 418 days.

(21) Appl. No.: 16/779,624

(22) Filed: Feb. 2, 2020

(65) Prior Publication Data

US 2021/0239599 A1 Aug. 5, 2021

(51) Int. Cl.
*G01N 17/00* (2006.01)
(52) U.S. Cl.
CPC ................. *G01N 17/004* (2013.01)
(58) Field of Classification Search
CPC ... G01N 17/004; G01N 21/88; G01N 2201/08
See application file for complete search history.

(56) References Cited

U.S. PATENT DOCUMENTS

| | | | | |
|---|---|---|---|---|
| 4,581,527 A | * | 4/1986 | Crane | G01M 11/086 385/13 |
| 6,720,550 B2 | * | 4/2004 | Bennett | G01D 5/3537 250/227.16 |
| 9,970,969 B1 | * | 5/2018 | Farrington | G01N 33/246 |
| 10,066,968 B2 | * | 9/2018 | Mekid | G01D 5/268 |
| 2005/0067559 A1 | * | 3/2005 | Ogisu | G01M 11/086 250/227.14 |
| 2008/0025664 A1 | * | 1/2008 | De Smet | G01N 21/552 385/13 |
| 2013/0050685 A1 | * | 2/2013 | Hunt | B82Y 15/00 356/73.1 |
| 2013/0202488 A1 | * | 8/2013 | Langer | G01N 21/41 422/69 |
| 2021/0148832 A1 | * | 5/2021 | Kvryan | G01N 17/04 |

* cited by examiner

*Primary Examiner* — Natalie Huls
(74) *Attorney, Agent, or Firm* — McDonnell Boehnen Hulbert & Berghoff LLP

(57) ABSTRACT

A method for testing physical properties of a material includes inserting coherent light into a waveguide such that the coherent light exits the waveguide at an end of the waveguide that is embedded within the material, thereby causing the coherent light to interact with the material. The method also includes detecting a reaction of the material to the coherent light.

20 Claims, 15 Drawing Sheets

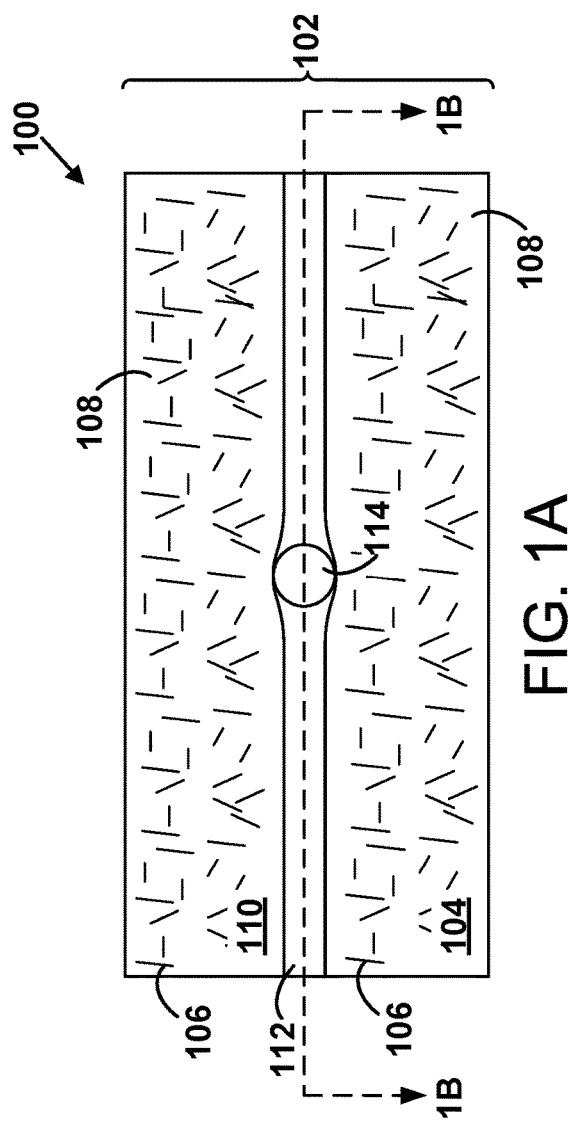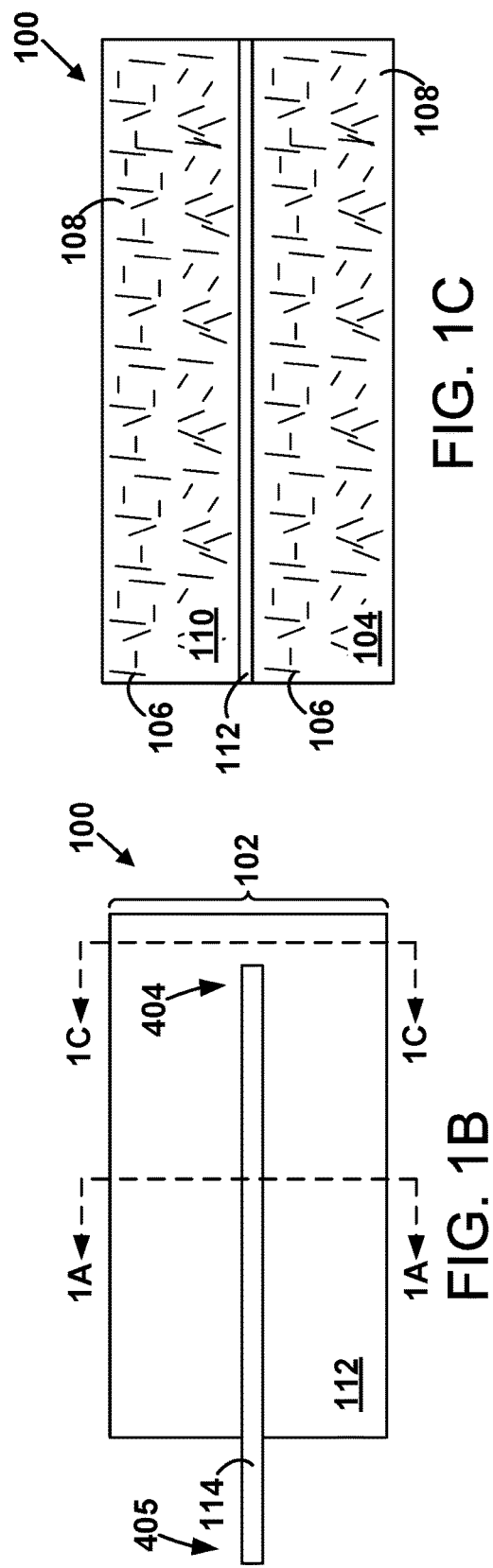

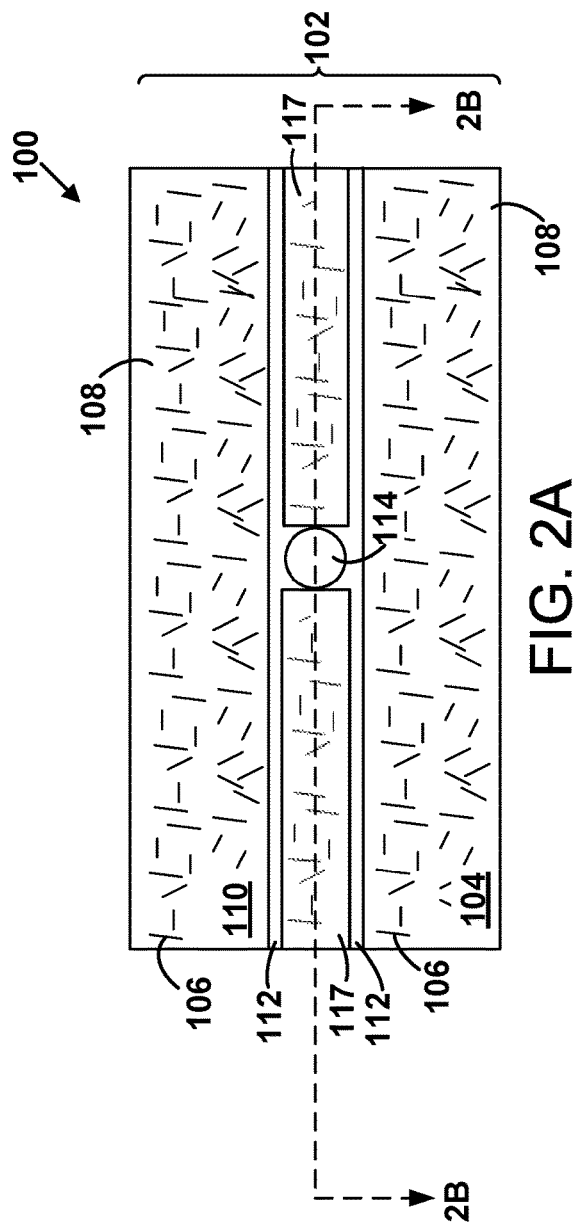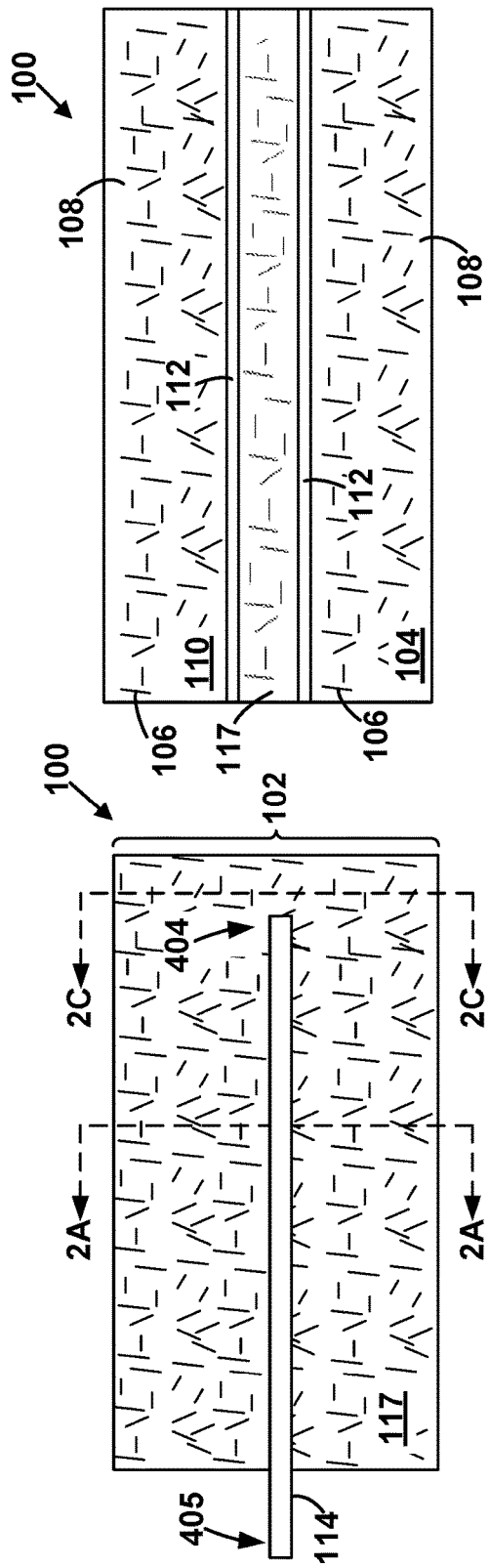

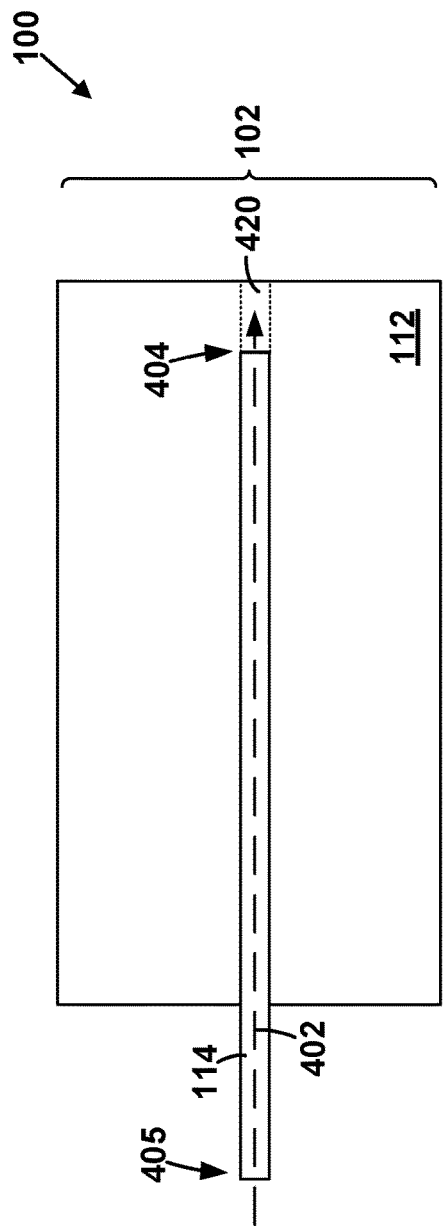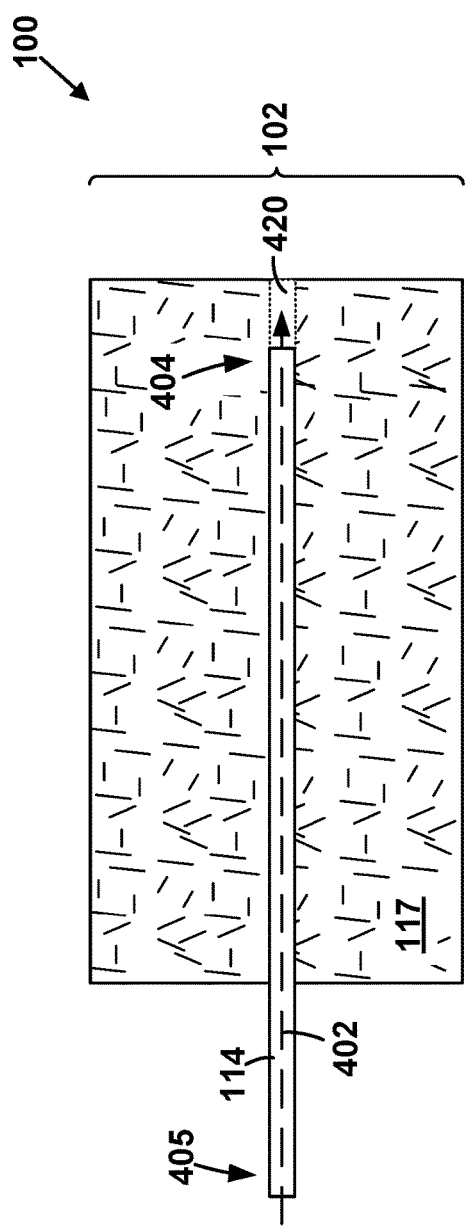

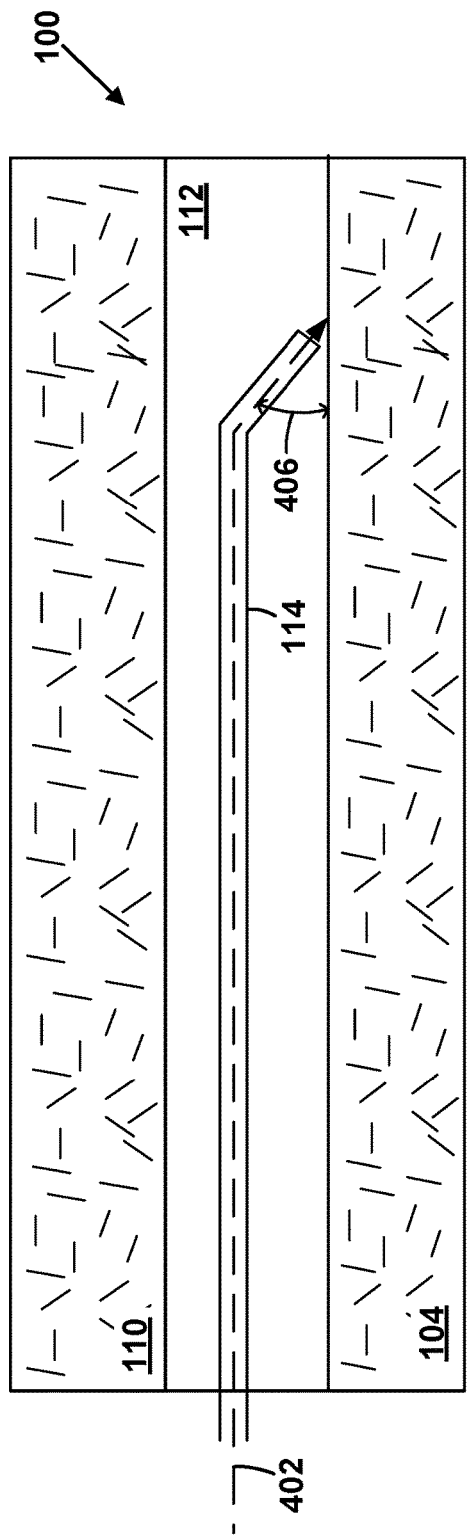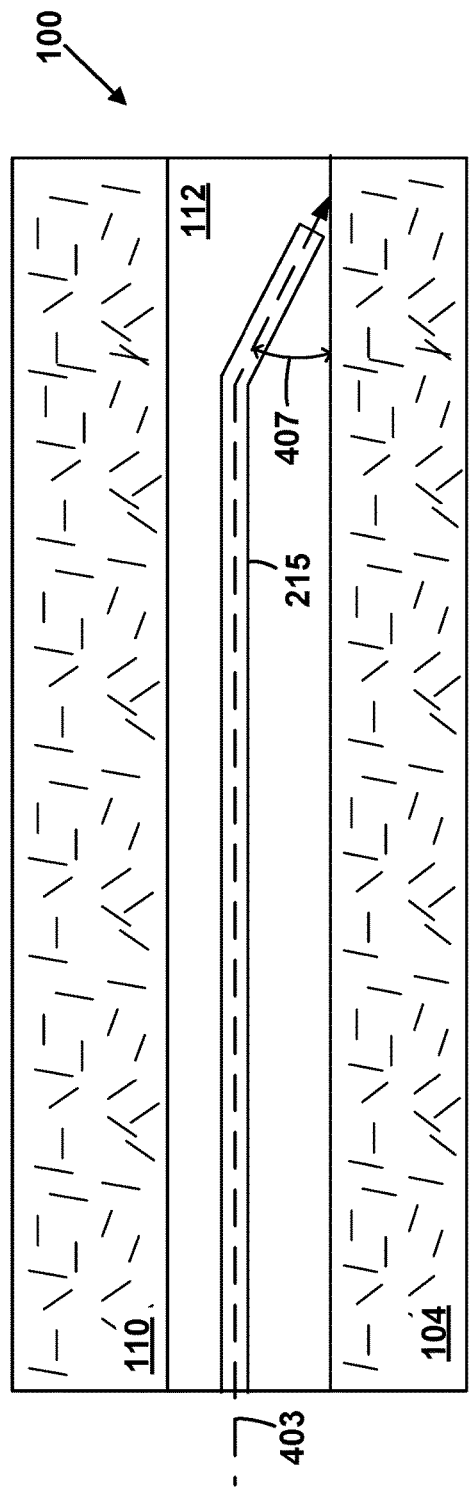

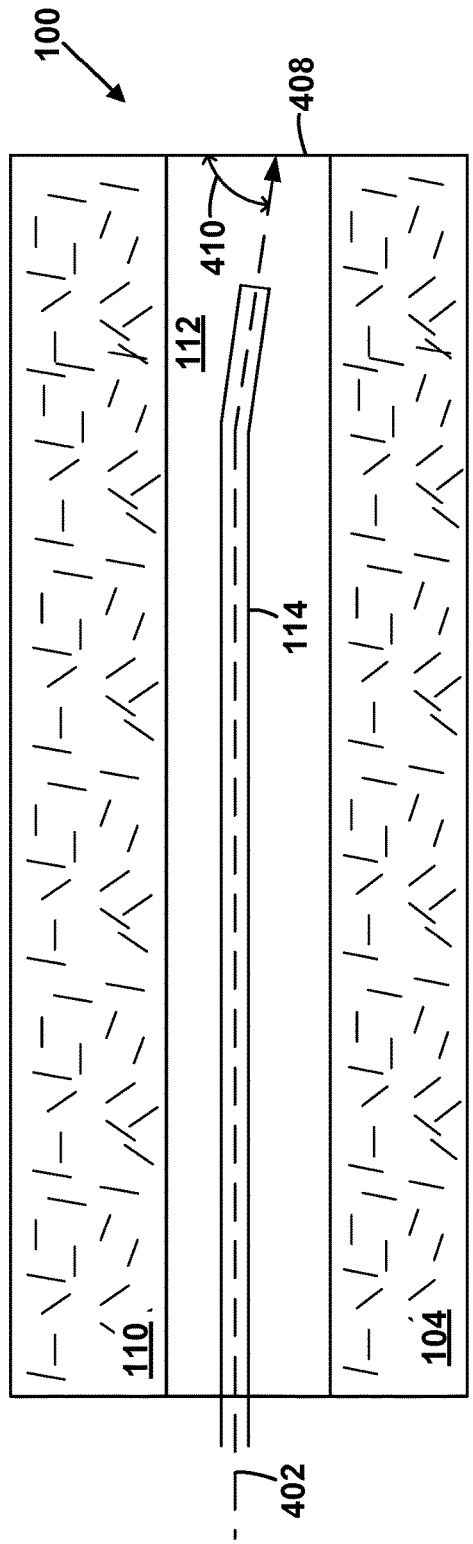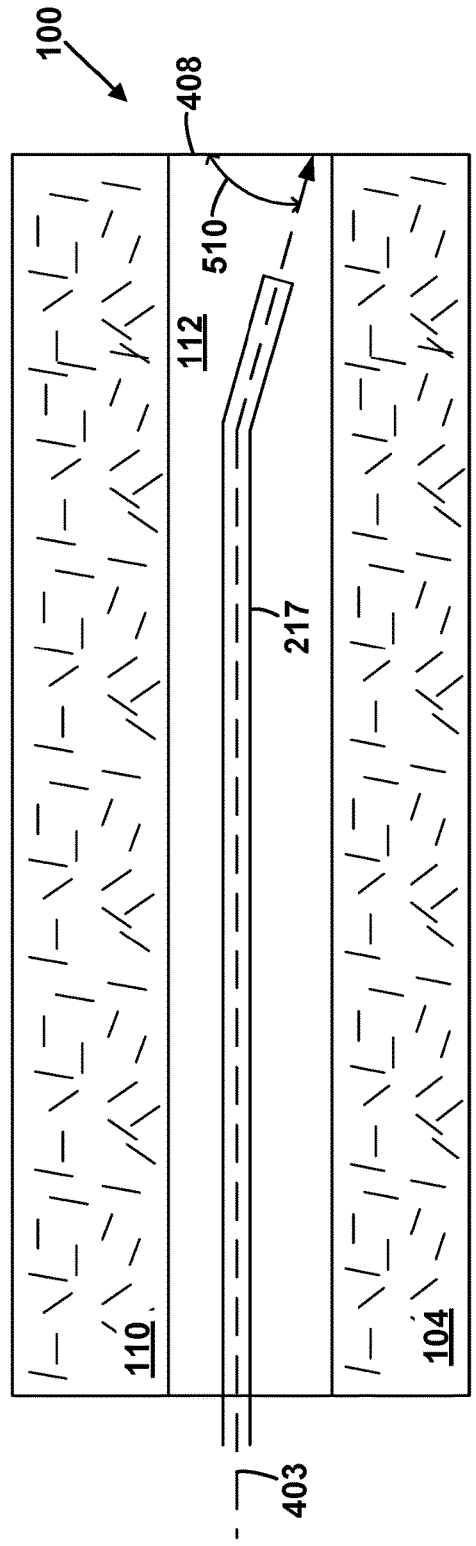
FIG. 5A
FIG. 5B

```
┌─────────────────────────────────────────────────────────┐
│ INSERTING COHERENT LIGHT INTO A WAVEGUIDE SUCH THAT THE │
│ COHERENT LIGHT EXITS THE WAVEGUIDE AT AN END OF THE     │
│ WAVEGUIDE THAT IS EMBEDDED WITHIN THE MATERIAL,         │
│ THEREBY CAUSING THE COHERENT LIGHT TO INTERACT WITH     │
│ THE MATERIAL                                            │
└─────────────────────────────────────────────────────────┘
         302
                              │
                              ▼
┌─────────────────────────────────────────────────────────┐
│ DETECTING A REACTION OF THE MATERIAL TO THE COHERENT    │
│                         LIGHT                           │
└─────────────────────────────────────────────────────────┘
     304
                                                      300

FIG. 9
```

```
┌─────────────────────────────────────────────────────────┐
│ INSERTING SECOND COHERENT LIGHT INTO A SECOND           │
│ WAVEGUIDE SUCH THAT THE SECOND COHERENT LIGHT           │
│ IMPINGES THE FIRST LAYER OF FIBROUS MATERIAL AT A SECOND│
│ ANGLE THAT IS UNEQUAL TO THE FIRST ANGLE                │
└─────────────────────────────────────────────────────────┘
     306
                                                      400

FIG. 10
```

INSERTING SECOND COHERENT LIGHT INTO A SECOND WAVEGUIDE SUCH THAT THE SECOND COHERENT LIGHT IMPINGES THE EDGE AT A SECOND ANGLE THAT IS UNEQUAL TO THE FIRST ANGLE

INSERTING SECOND COHERENT LIGHT INTO A SECOND WAVEGUIDE SUCH THAT THE SECOND COHERENT LIGHT EXITS THE SECOND WAVEGUIDE AT A SECOND END OF THE SECOND WAVEGUIDE THAT IS EMBEDDED WITHIN THE MATERIAL, THEREBY CAUSING THE SECOND COHERENT LIGHT TO INTERACT WITH THE MATERIAL, WHEREIN THE SECOND COHERENT LIGHT HAS A SECOND OSCILLATION FREQUENCY THAT IS UNEQUAL TO THE FIRST OSCILLATION FREQUENCY

310

DETECTING A SECOND REACTION OF THE MATERIAL TO THE SECOND COHERENT LIGHT

INSERTING SECOND COHERENT LIGHT INTO A SECOND WAVEGUIDE SUCH THAT THE SECOND COHERENT LIGHT EXITS THE SECOND WAVEGUIDE AT A SECOND END OF THE SECOND WAVEGUIDE THAT IS EMBEDDED WITHIN THE MATERIAL, THEREBY CAUSING THE SECOND COHERENT LIGHT TO INTERACT WITH THE MATERIAL, WHEREIN THE SECOND END OF THE SECOND WAVEGUIDE IS SEPARATED FROM THE EDGE OF THE MATERIAL BY A SECOND DISTANCE THAT IS UNEQUAL TO THE FIRST DISTANCE

320

DETECTING A SECOND REACTION OF THE MATERIAL TO THE SECOND COHERENT LIGHT

TEST FIXTURE AND METHOD FOR USE

FIELD

The present disclosure generally relates to methods and test fixtures for testing physical properties of a material, and more specifically to methods and test fixtures for testing physical properties of a composite material.

BACKGROUND

Composite materials such as those used for the formation of aircraft structural components can be subjected to a wide variety of stresses while in use. For example, electrical discharge from the atmosphere or from other sources can cause high levels of electrical current to pass through a composite material. This can cause the physical properties of the composite material to undesirably change and/or cause undesirable ejection of hot particles or gas. Thus, it is useful to test such composite materials prior to installation as aircraft structural components to ascertain the effects of such stresses upon the composite material.

One conventional method for testing composite materials includes inserting two electrical probes into the composite material and using an electrical power supply to drive current through the material via the probes. When using this method, it is difficult to precisely control where the current flows within the material for at least the reason that the electrical field generated by the probes is three-dimensional. That is, the current will take a number of paths when travelling from one probe to the other. Composite material can also be inspected after such stress incidents occur in the field, although it is much more desirable to ascertain the properties of the composite material prior to installation. Additionally, the information obtainable from such post-incident inspection is limited because it is difficult to quantify the stress (e.g., the current) that the composite material experienced.

As such, a need exists for methods and test fixtures that can be used to obtain more specific and localized information about how composite materials react to stresses prior to installation of such materials.

SUMMARY

One aspect of the disclosure is a method for testing physical properties of a material, the method comprising: inserting coherent light into a waveguide such that the coherent light exits the waveguide at an end of the waveguide that is embedded within the material, thereby causing the coherent light to interact with the material; and detecting a reaction of the material to the coherent light.

Another aspect of the disclosure is a method of forming a test fixture for testing physical properties of a material, the method comprising: forming a first layer of a fibrous material, the fibrous material comprising fibers embedded within a matrix material; forming a second layer of the fibrous material; and forming a resin layer between the first layer and the second layer such that a waveguide is embedded within the resin layer.

A further aspect of the disclosure is a test fixture for testing physical properties of a material, the test fixture comprising: a first layer of a fibrous material, the fibrous material comprising fibers embedded within a matrix material; a second layer of the fibrous material; a resin layer between the first layer of the fibrous material and the second layer of the fibrous material; and a waveguide embedded within the resin layer.

By the term "about" or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

The features, functions, and advantages that have been discussed can be achieved independently in various examples or may be combined in yet other examples further details of which can be seen with reference to the following description and drawings.

BRIEF DESCRIPTION OF THE DRAWINGS

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying Figures.

FIG. 1A is a cross sectional view of a test fixture for testing physical properties of a material, according to an example.

FIG. 1B is a cross sectional view of a test fixture for testing physical properties of a material, according to an example.

FIG. 1C is a cross sectional view of a test fixture for testing physical properties of a material, according to an example.

FIG. 2A is a cross sectional view of a test fixture for testing physical properties of a material, according to an example.

FIG. 2B is a cross sectional view of a test fixture for testing physical properties of a material, according to an example.

FIG. 2C is a cross sectional view of a test fixture for testing physical properties of a material, according to an example.

FIG. 3A schematically depicts functionality related to a test fixture, according to an example.

FIG. 3B schematically depicts functionality related to a test fixture, according to an example.

FIG. 4A schematically depicts functionality related to a test fixture, according to an example.

FIG. 4B schematically depicts functionality related to a test fixture, according to an example.

FIG. 5A schematically depicts functionality related to a test fixture, according to an example.

FIG. 5B schematically depicts functionality related to a test fixture, according to an example.

FIG. 9 is a block diagram of a method, according to an example.

FIG. 10 is a block diagram of a method, according to an example.

FIG. 11 is a block diagram of a method, according to an example.

FIG. 12 is a block diagram of a method, according to an example.

FIG. 16 is a block diagram of a method, according to an example.

DETAILED DESCRIPTION

Figure 3C:
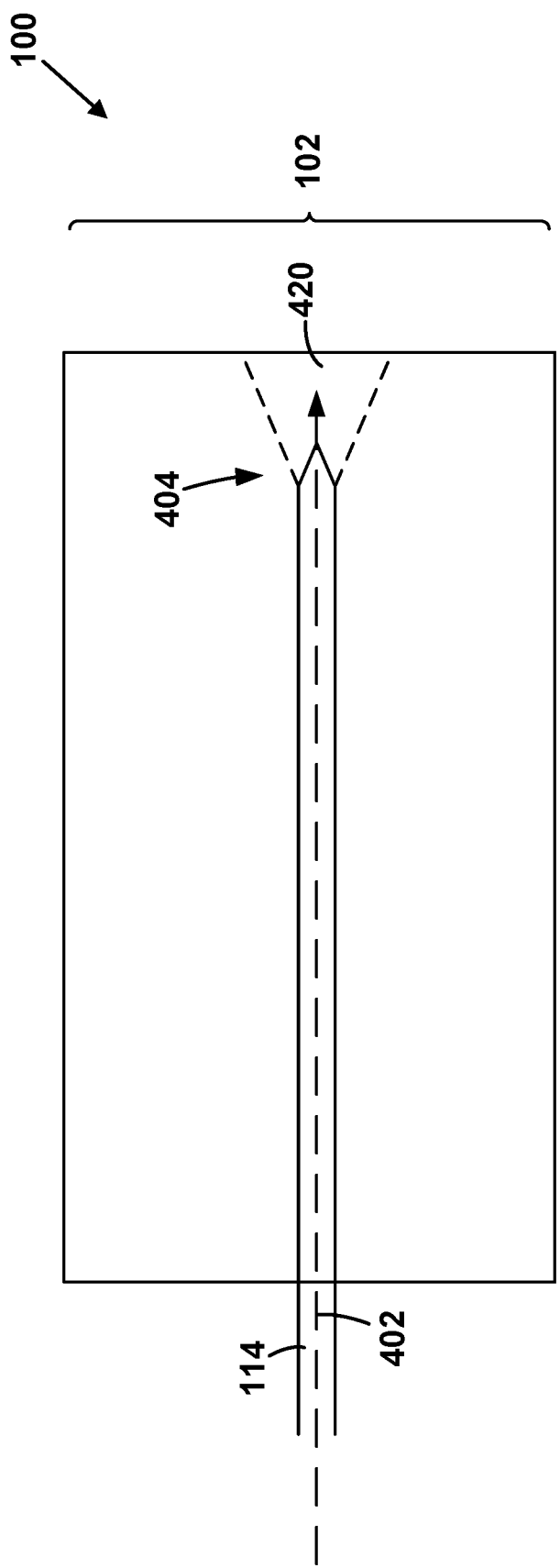
FIG. 3C schematically depicts functionality related to a test fixture, according to an example.

As discussed above, there exists a need for methods and test fixtures that can be used to obtain specific, detailed, and localized information about how composite materials react to stresses prior to installation of such materials. Within examples, a method for testing physical properties of a material includes inserting coherent light (e.g., collimated laser light) into a waveguide (e.g., a fiber optic cable) such that the coherent light exits the waveguide at an end of the waveguide that is embedded within the material, thereby causing the coherent light to interact with the material. The method also includes detecting a reaction of the material to the coherent light. Reactions of the material to the coherent light could include heating, phase change, disintegration, changes in electrical and/or thermal conductivity, emission of light, and/or ejection of hot particles or gas. Detection of such reactions could include capturing still images and/or video using infrared or visible light cameras, manual observation, and/or testing via a multimeter. Additionally or alternatively, the material could be immersed in or surrounded by a flammable gas and/or liquid and the presence or absence of ignition could be observed. Other examples are possible.

The aforementioned methods and test fixtures can be advantageous when compared to conventional methods and test fixtures because use of the aforementioned methods and test fixtures can involve better control of the location and the volume of the composite material that is affected by the applied stress (e.g., the coherent light). This can lead to more accurate quantification of the stress experienced by the composite material on a per volume basis. The disclosed methods can also be used to specifically test internal boundaries of the material (e.g., boundaries between layers of fibrous material that are joined by a resin layer) or external edges of the composite material. The observed reaction of the material to such stress can be used to determine whether the composite material is suitable for use in the field.

Disclosed examples will now be described more fully hereinafter with reference to the accompanying Drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

FIG. 1A is a cross sectional view of a test fixture 100 for testing physical properties of a material 102. The test fixture 100 includes a first layer 104 of a fibrous material. The fibrous material includes fibers 106 embedded within a matrix material 108. The test fixture 100 also includes a second layer 110 of the fibrous material and a resin layer 112 between the first layer 104 and the second layer 110. The test fixture 100 also includes a waveguide 114 embedded within the resin layer 112.

The test fixture 100 includes the material 102. The material 102 includes the first layer 104, the second layer 110, and the resin layer 112.

The first layer 104 includes the fibers 106 and the matrix material 108. The fibers 106 are embedded in the matrix material 108. The fibers 106 are typically carbon fibers, ceramic fibers, cellulosic fibers, or glass fibers, and the matrix material 108 is typically cured thermoplastic or cured thermoset. The second layer 110 also includes the fibers 106 and the matrix material 108.

The resin layer 112 can include a cured epoxy resin or a thermoplastic, but other examples are possible. In some examples, the resin layer 112 has substantially similar material content as the matrix material 108. The resin layer 112 can be used to bond the first layer 104 to the second layer 110. In some embodiments, the material includes numerous alternating layers of fibrous material and resin material, with the layers of resin material being used to bond layers of fibrous material to other layers of fibrous material to form a somewhat periodic sandwich structure. The relative dimensions or thicknesses of the resin layer 112, the first layer 104, and the second layer 110 are not necessarily shown to scale in FIG. 1A, FIG. 1B, or FIG. 1C.

The waveguide 114 typically takes the form of a glass or plastic fiber optic cable, but other examples are possible. A sapphire fiber optic cable could be used as well. As shown, the waveguide 114 is embedded within the resin layer 112 and is between the first layer 104 and the second layer 110.

FIG. 1B is another cross sectional view of the test fixture 100. As shown, a first end 404 of the waveguide 114 is embedded within the material 102 and a second end 405 of the waveguide 114 is outside of the material 102. The relative dimensions or thicknesses of the waveguide 114 and the material 102 are not necessarily shown to scale.

FIG. 1C is another cross sectional view of the test fixture 100. The cross section of the material shown by FIG. 1C is beyond the first end 404 of the waveguide 114 that is embedded in the material 102. As shown, the thickness of the resin layer 112 can be reduced in the absence of the waveguide 114 when compared to the section of the test fixture 100 shown in FIG. 1A.

The test fixture 100 can be formed, in part, by forming the first layer 104. Forming the first layer 104 generally involves forming a mixture of the fibers 106 and an uncured viscous or liquid version of the matrix material 108. In some examples, a pre-formed and/or woven strip of the fibers 106 can be embedded within the uncured viscous or liquid version of the matrix material 108. Thereafter, the mixture is cured and the matrix material 108 is hardened to form the first layer 104. The first layer 104 can also be formed via curing a pre-impregnated sheet of carbon fibers or unidirectional ply sheet(s) of carbon fiber material.

The test fixture 100 can additionally be formed by forming the second layer 110. The second layer 110 can be formed similarly to how the first layer 104 is formed.

The test fixture 100 can additionally be formed by forming the resin layer 112 between the first layer 104 and the second layer 110 such that the waveguide 114 is embedded within the resin layer 112. For example, an uncured resin material that is to make up the resin layer 112 can be poured, spread, injected, or otherwise positioned on the first layer 104. The waveguide 114 can be placed on the first layer 104 before or after placing the uncured resin material onto the first layer 104. After positioning the waveguide 114 within the uncured resin material, the second layer 110 is brought into contact with the uncured resin material and/or the waveguide 114. Next, the uncured resin material is heated or otherwise cured to form the resin layer 112. As such, the waveguide 114 is embedded within the resin layer 112 between the first layer 104 and the second layer 110.

In some examples, the resin layer 112 is formed during curing via diffusion of some of the matrix material 108 into an area between the first layer 104 and the second layer 110, for example when the first layer 104 and/or the second layer 110 are formed from a pre-impregnated sheet of carbon fiber or unidirectional ply sheet(s) of carbon fiber material.

FIG. 2A, FIG. 2B, and FIG. 2C show another embodiment of the test fixture 100. FIG. 2A is a cross sectional view of the test fixture 100. The test fixture 100 includes the first layer 104 of the fibrous material. The test fixture 100 also includes the second layer 110 of the fibrous material and the resin layer 112 between the first layer 104 and the second layer 110. The test fixture 100 also includes the waveguide 114 embedded within the resin layer 112.

One difference when compared to the embodiment shown in FIG. 1A, FIG. 1B, and FIG. 1C is that the embodiment shown in FIG. 2A, FIG. 2B, and FIG. 2C also includes a third layer 117 of the fibrous material in addition to the layers of the fibrous material that are discussed above.

As shown in the cross section of FIG. 2A, the third layer 117 bookends the waveguide 114. That is, the third layer 117 is on a left side of the waveguide 114 and on a right side of the waveguide 114. In addition to being between the first layer 104 and the second layer 110, the resin layer 112 is also between the third layer 117 and the first layer 104 and between the third layer 117 and the second layer 110.

FIG. 2B is another cross sectional view of the test fixture 100 shown in FIG. 2A. As shown, the first end 404 of the waveguide 114 is embedded within the material 102 and the second end 405 of the waveguide 114 is outside of the material 102. The relative dimensions or thicknesses of the waveguide 114 and the material 102 are not necessarily shown to scale.

FIG. 2C is another cross sectional view of the test fixture 100. The cross section of the material 102 shown by FIG. 2C is beyond the first end 404 of the waveguide 114 that is embedded in the material 102. As shown in the cross section of FIG. 2C, the third layer 117 is not interrupted by the waveguide 114 as in the cross section shown in FIG. 2A.

The test fixture 100 shown in FIG. 2A, FIG. 2B, and FIG. 2C can be formed, in part, by forming the first layer 104. Forming the first layer 104 generally involves forming a mixture of the fibers 106 and an uncured viscous or liquid version of the matrix material 108. In some examples, a pre-formed and/or woven strip of the fibers 106 can be embedded within the uncured viscous or liquid version of the matrix material 108. Thereafter, the mixture is cured and the matrix material 108 is hardened to form the first layer 104.

The test fixture 100 can additionally be formed by forming the second layer 110. The second layer 110 can be formed similarly to how the first layer 104 is formed.

The test fixture 100 can additionally be formed by forming the third layer 117. The third layer 117 can be formed similarly to how the first layer 104 and/or the second layer 110 are formed, however, after formation a strip-shaped portion is cut out of or otherwise removed from the third layer 117 to accommodate the waveguide as shown in FIG. 2A and FIG. 2B.

The test fixture 100 can additionally be formed by forming the resin layer 112 between the first layer 104 and the second layer 110 such that the waveguide 114 is embedded within the resin layer 112. More specifically, one can form the resin layer 112 between the first layer 104 and the third layer 117 and between the third layer 117 and the second layer 110. For example, an uncured resin material that is to make up the resin layer 112 can be poured, spread, or otherwise positioned on the first layer 104. The waveguide 114 can be placed on the first layer 104 before or after placing the uncured resin material onto the first layer 104.

Additionally, the third layer 117 is placed on the uncured resin material (e.g., on the first layer 104) such that it surrounds the waveguide 114 on three sides as shown in FIG. 2B. The waveguide 114 can be placed on the first layer 104 and on the uncured resin material before or after the third layer 117 is placed on the uncured resin material and/or the first layer 104.

After positioning the waveguide 114 and the third layer 117 on and/or within the uncured resin material, the second layer 110 is brought into contact with the uncured resin material, the third layer 117, and/or the waveguide 114. Next, the uncured resin material is heated or otherwise cured to form the resin layer 112. As such, the waveguide 114 is embedded within the resin layer 112 between the first layer 104 and the second layer 110 and surrounded by the third layer 117 on three sides as shown in FIG. 2B.

FIG. 3A schematically depicts functionality related to the test fixture 100 shown in FIGS. 1A-1C. The first end 404 of the waveguide 114 is embedded within the material 102 (e.g., the resin layer 112), whereas the second end 405 of the waveguide 114 extends outside of the material 102 (e.g., the resin layer 112). The first end 404 is embedded within the resin layer 112 and between the first layer of the fibrous material and the second layer of the fibrous material.

FIG. 3B schematically depicts functionality related to the test fixture 100 shown in FIGS. 2A-2C. The first end 404 of the waveguide 114 is embedded within the material 102 (e.g., the resin layer), whereas the second end 405 of the waveguide 114 extends outside of the material 102 (e.g., the resin layer). The waveguide 114 shown in FIG. 3B is also surrounded by the third layer 117 on three sides. The first end 404 is embedded within the resin layer and between the first layer of the fibrous material and the second layer of the fibrous material.

The following description applies to the embodiment of the test fixture 100 shown in FIG. 3A and to the embodiment of the test fixture 100 shown in FIG. 3B. To test physical properties of the material 102, one can optically couple the second end 405 to a source of coherent light 402 (e.g., a laser) and insert the coherent light 402 into the waveguide 114 such that the coherent light 402 propagates through the waveguide 114 and exits the waveguide 114 at the first end 404, thereby interacting with the material 102. More specifically, the coherent light 402 can interact with the first layer of the fibrous material that is below the resin layer 112, the second layer of the fibrous material that is above the resin layer 112, the third layer 117 of the fibrous material (if present) that is between the first layer and the second layer, and/or the resin layer 112.

In some embodiments, the coherent light 402 interacts substantially exclusively with a volume 420 of the material 102 that is less than an entirety of the material 102. By controlling the volume 420 of the material 102 that the coherent light 402 interacts with, one can induce adiabatic heating of the volume 420 of the material 102. In this way, the test fixture 100 can be used to test a localized and quantifiable portion of the material 102. For example, a theoretical model can be used to simulate stress conditions in a localized portion of the material and the test fixture 100 can be used to experimentally quantify the reaction of the material to the stress for comparison to the model.

Additionally, a transverse cross section of the volume 420 (e.g., within a plane perpendicular to the page) can have a first shape that is substantially equivalent to a second shape of the first end 404 of the waveguide 114. For example, both the first end 404 and the volume 420 could have cross sectional shapes that are circles, ellipses, squares, etc.

A reaction of the material 102 to the coherent light 402 can be detected by capturing still images and/or video using infrared or visible light cameras, manual observation, and/or testing via a multimeter. Additionally or alternatively, the material could be immersed in or surrounded by a flammable gas and/or liquid and the presence or absence of ignition could be observed. Accordingly, detecting the reaction can include one or more of detecting light that is emitted from the material 102, detecting ejection of one or more particles from the material 102, detecting a change in physical properties of the material 102, or ejection of gas from the material 102. More specifically, the infrared or visible light cameras can be used to capture light emitted from the material, detect particle ejection, or detect gas ejection. Manual inspection or a multimeter could be used to detect changes in physical properties such as hardness, electrical conductivity, or thermal conductivity. Other examples are possible.

FIG. 3C schematically depicts functionality related to the test fixture 100 shown in FIGS. 1A-1C and FIGS. 2A-2C. In FIG. 3C, the waveguide 114 has a first end 404 that is cleaved to form a conical shape. As such, the coherent light 402 interacts substantially exclusively with a volume 420 of the material 102 that is less than an entirety of the material 102. In this example, the volume 420 is also cone-shaped, but other shapes are possible and would be at least partially defined by the shape of the first end 404.

FIG. 4A and FIG. 4B schematically depict functionality related to the test fixture 100 shown in FIGS. 1A-1C and in FIGS. 2A-C. In FIG. 4A, the coherent light 402 is inserted into the waveguide 114, which has an elbow that causes the coherent light 402 to impinge the first layer 104 at an angle 406.

FIG. 4B shows the same test fixture 100 as in FIG. 4A, but at a cross section that is parallel to the cross section shown in FIG. 4A. In FIG. 4B, coherent light 403 is inserted into a waveguide 215, which has an elbow that causes the coherent light 403 to impinge the first layer 104 at an angle 407 that is different from the angle 406. Differences in the reactions respectively caused by the coherent light 402 and the coherent light 403 can be used in further study of the material, including the first layer 104 and the resin layer 112. In some examples, the coherent light 402 and the coherent light 403 could have similar or identical characteristics except for respective impingement angles, so that any effect of the impingement angle on the reaction of the material can be isolated and characterized.

FIG. 5A and FIG. 5B schematically depict functionality related to the test fixture 100 shown in FIGS. 1A-1C and in FIGS. 2A-C. In FIG. 5A, the waveguide 114 has an elbow that causes the coherent light 402 to impinge an edge 408 of the material at an angle 410. FIG. 5B shows the same test fixture 100 as in FIG. 5A, but at a cross section that is parallel to the cross section shown in FIG. 5A. In FIG. 5B, the coherent light 403 is inserted into a waveguide 217. The waveguide 217 has an elbow that causes the coherent light 403 to impinge the edge 408 at an angle 510 that is different from the angle 410. Differences in the reactions respectively caused by the coherent light 402 and the coherent light 403 can be used in further study of the material, including the resin layer 112. In some examples, the coherent light 402 and the coherent light 403 could have similar or identical characteristics except for respective impingement angles, so that any effect of the impingement angle on the reaction of the material can be isolated and characterized.

Figure 6:
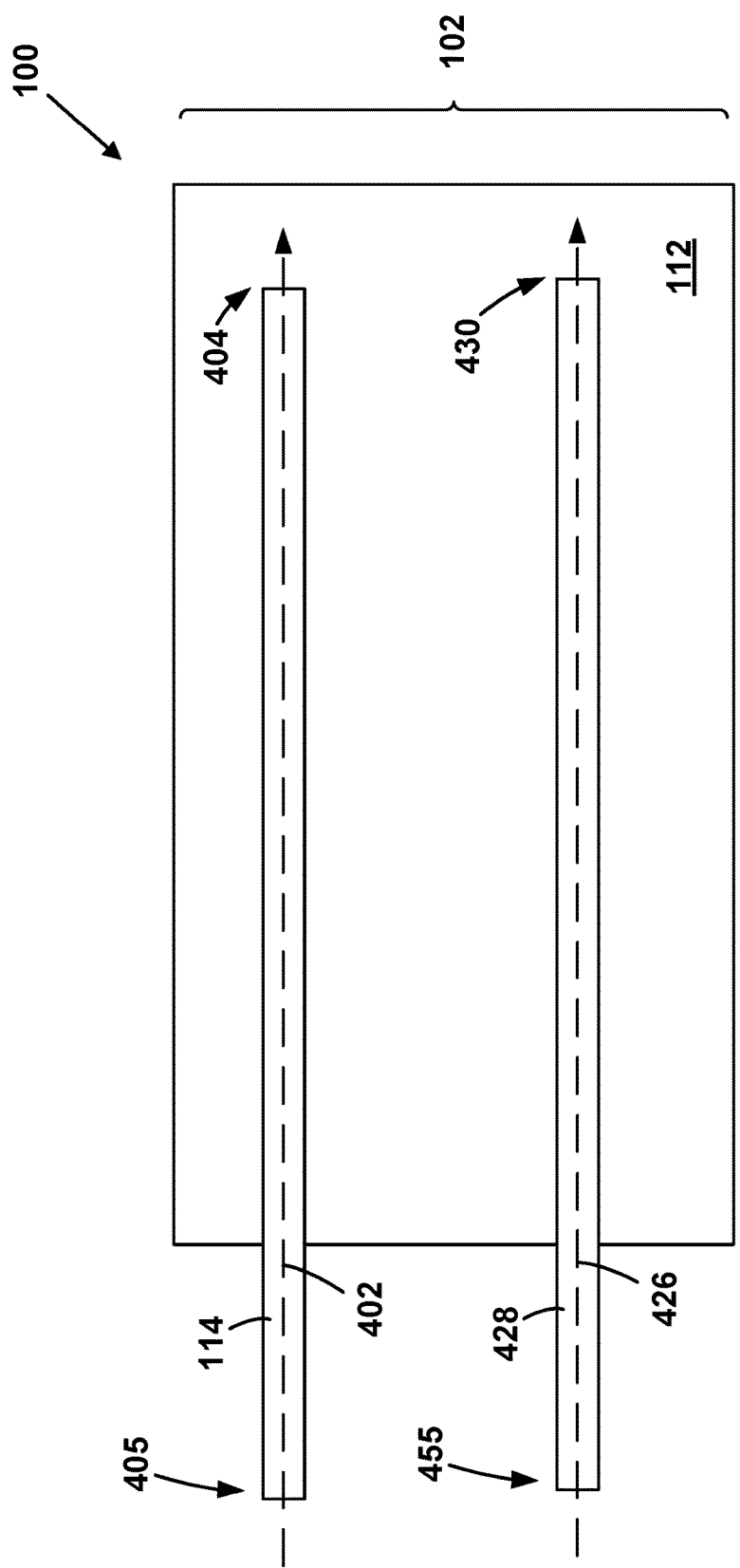
FIG. 6 schematically depicts functionality related to a test fixture, according to an example.

FIG. 6 schematically depicts functionality related to the test fixture 100 shown in FIGS. 1A-1C and in FIGS. 2A-C. The coherent light 402 is inserted into the waveguide 114 at the second end 405 and exits the waveguide 114 at the first end 404 that is embedded within the material 102. Also, coherent light 426 is inserted into a waveguide 428 at an end 455 and exits the waveguide 428 at an end 430 that is embedded within the material 102, thereby causing the coherent light 426 to interact with the material 102. In this example, the coherent light 402 has an oscillation frequency $f_1$ and the coherent light 426 has an oscillation frequency $f_2$ that is different than $f_1$. Otherwise, the coherent light 402 and the coherent light 426 might have similar or identical characteristics so that any effect of the difference in frequency on the reaction of the material 102 can be isolated and characterized.

In another embodiment, the coherent light 402 is characterized by a first pulse rise time and the coherent light 426 is characterized by a second pulse rise time. For example, the first rise time could be the time between an instantaneous power of the coherent light 402 transitioning from 10% to 90% of a maximum value of the instantaneous power of the coherent light 402. Similarly, the second rise time could be the time between an instantaneous power of the coherent light 426 transitioning from 10% to 90% of a maximum value of the instantaneous power of the coherent light 426. In this example, the second pulse rise time is different from the first pulse rise time. Otherwise, the coherent light 402 and the coherent light 426 might have similar or identical characteristics so that any effect of the difference in pulse rise time on the reaction of the material 102 can be isolated and characterized.

In another embodiment, the coherent light 402 is characterized by a first peak power and the coherent light 426 is characterized by a second peak power. For example, the first peak power could be a maximum of the instantaneous power of the coherent light 402. Similarly, the second peak power could be a maximum of the instantaneous power of the coherent light 426. In this example, the second peak power is different from the first peak power. Otherwise, the coherent light 402 and the coherent light 426 might have similar or identical characteristics so that any effect of the difference in peak power on the reaction of the material 102 can be isolated and characterized.

In another embodiment, the coherent light 402 is characterized by a first energy dose and the coherent light 426 is characterized by a second energy dose. For example, the first energy dose could be a total amount of energy included in a single pulse of the coherent light 402. Similarly, the second energy dose could be a total amount of energy included in a single pulse of the coherent light 426. In this example, the second energy dose is different from the first energy dose. Otherwise, the coherent light 402 and the coherent light 426 might have similar or identical characteristics so that any effect of the difference in energy dose on the reaction of the material 102 can be isolated and characterized.

Figure 7:
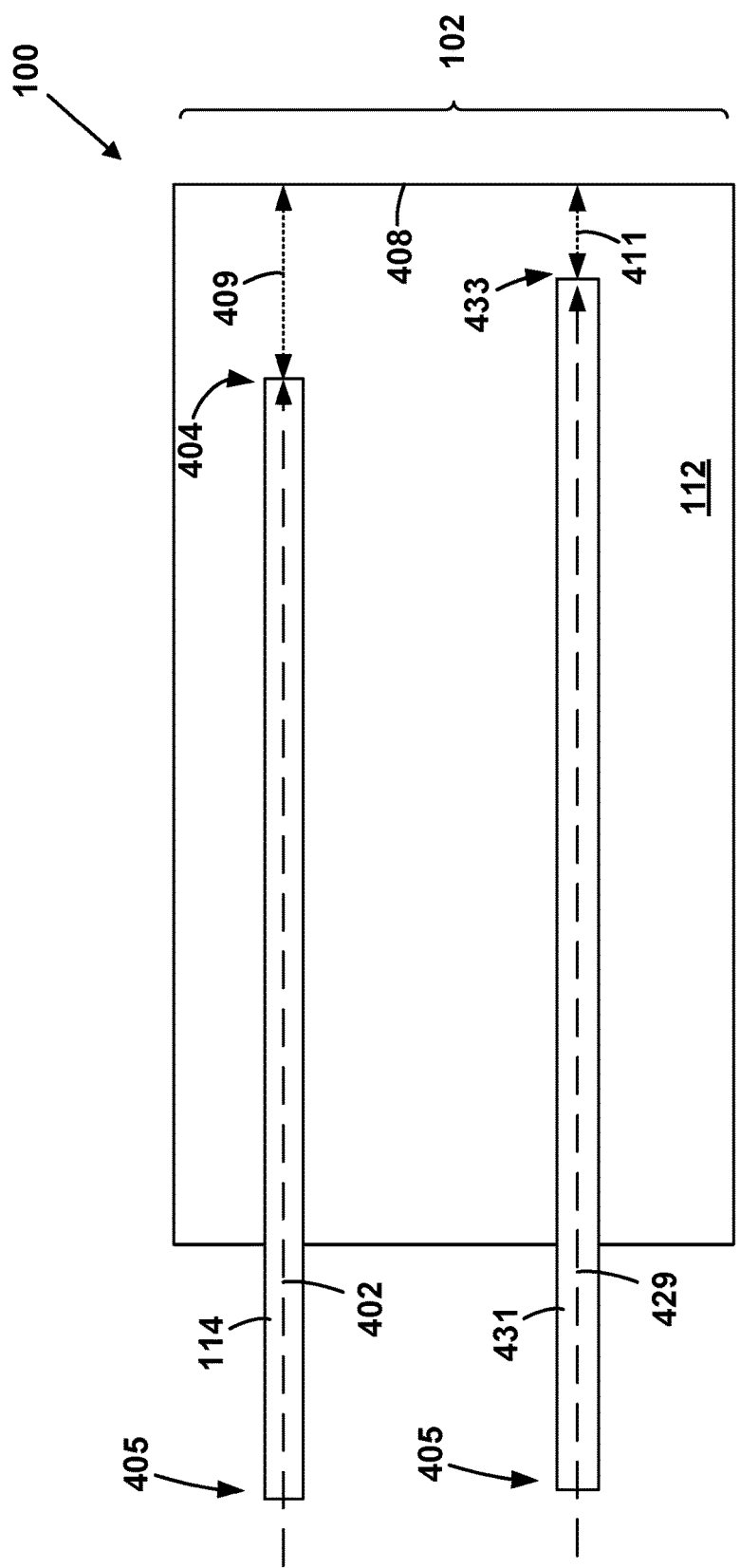
FIG. 7 schematically depicts functionality related to a test fixture, according to an example.

FIG. 7 schematically depicts functionality related to the test fixture 100 shown in FIGS. 1A-1C and in FIGS. 2A-C. The end 404 of the waveguide 114 is separated from the edge 408 of the material 102 by a first distance 409.

Coherent light 429 is inserted into a waveguide 431 such that the coherent light 429 exits the waveguide 431 at an end 433 of the waveguide 431 that is embedded within the material 102, thereby causing the coherent light 429 to interact with the material 102. The end 433 is separated from the edge 408 by a distance 411 that is unequal to the distance 409. The coherent light 402 and the coherent light 429 might have similar or identical characteristics so that any effect of the difference in waveguide end distance to the edge 408 on the reaction of the material 102 can be isolated and characterized.

Figure 8:
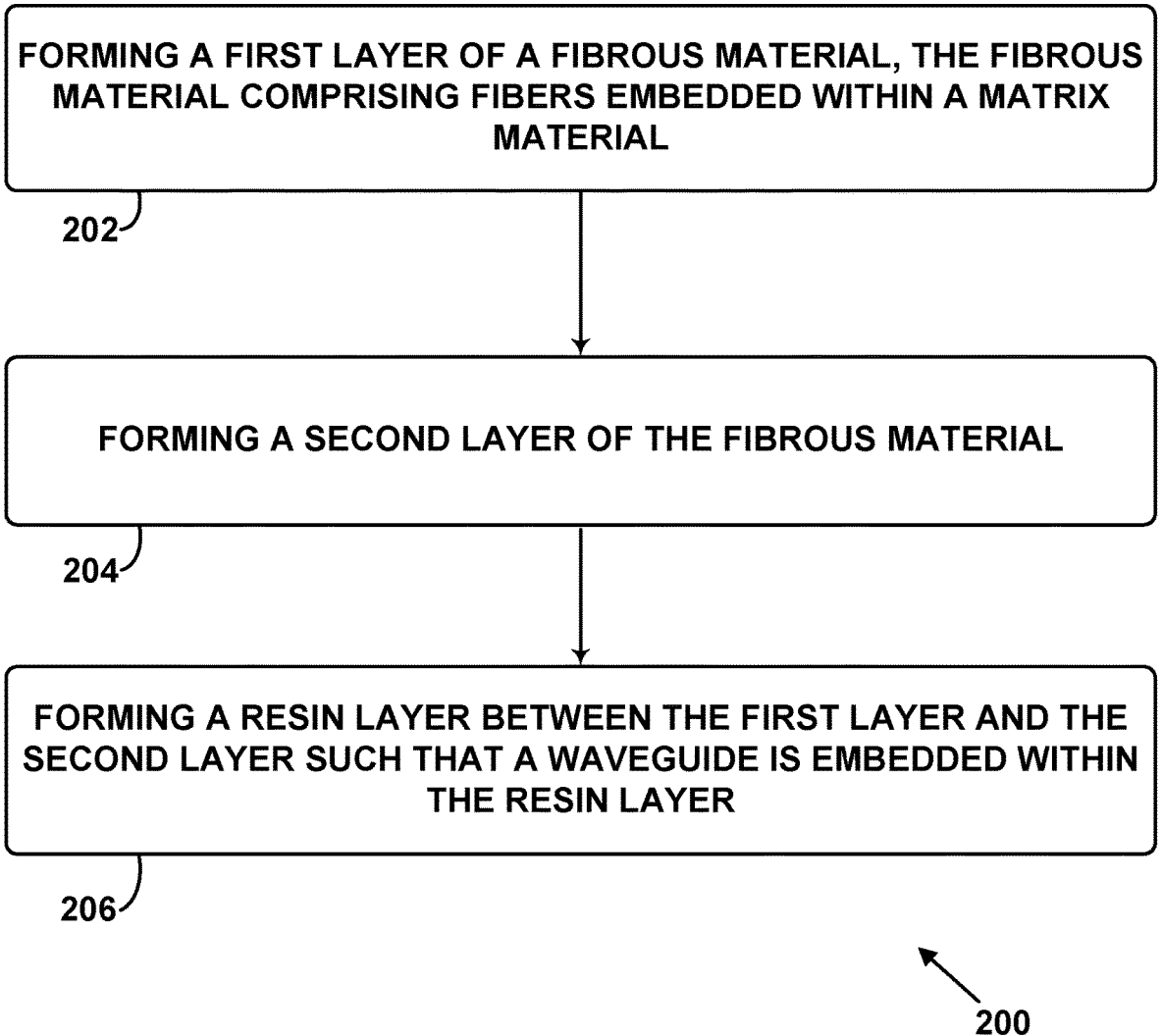
FIG. 8 is a block diagram of a method, according to an example.

FIG. 8 is a block diagram of a method 200 of forming the test fixture 100 for testing physical properties of the material 102, according to example implementations. FIGS. 9-16 are block diagrams of methods 300, 400, 500, 600, 700, 800, 900, and 950 for testing physical properties of the material 102. The methods 300, 400, 500, 600, 700, 800, 900, and 950 present examples of methods that could be used with the test fixture 100 as shown in FIGS. 3-7. As shown in FIGS. 8-16, the methods 200, 300, 400, 500, 600, 700, 800, 900, and 950 include one or more operations, functions, or actions as illustrated by blocks 202, 204, 206, 302, 304, 306, 308, 310, 312, 314, 316, 318, and 320. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

Referring to FIG. 8, at block 202 the method 200 includes forming the first layer 104 of the fibrous material, the fibrous material comprising the fibers 106 embedded within the matrix material 108.

At block 204, the method 200 includes forming the second layer 110 of the fibrous material.

At block 206, the method 200 includes forming the resin layer 112 between the first layer 104 and the second layer 110 such that the waveguide 114 is embedded within the resin layer 112.

Referring to FIG. 9, at block 302 the method 300 includes inserting the coherent light 402 into the waveguide 114 such that the coherent light 402 exits the waveguide 114 at the end 404 of the waveguide 114 that is embedded within the material 102, thereby causing the coherent light 402 to interact with the material 102.

At block 304, the method 300 includes detecting the reaction of the material 102 to the coherent light 402.

In some examples, the coherent light 402 is inserted such that the coherent light 402 impinges the first layer 104 of the fibrous material at the first angle 406. Referring to FIG. 10, at block 306 the method 400 includes inserting the second coherent light 403 into the second waveguide 215 such that the second coherent light 403 impinges the first layer 104 of the fibrous material at the second angle 407 that is unequal to the first angle 406.

In some examples, the coherent light 402 is inserted such that the coherent light 402 impinges the edge 408 of the material 102 at the first angle 410. Referring to FIG. 11, at block 308 the method 500 includes inserting the second coherent light 403 into the second waveguide 217 such that the second coherent light 403 impinges the edge 408 at the second angle 510 that is unequal to the first angle 410.

In some examples, the coherent light 402 has a first oscillation frequency $f_1$. Referring to FIG. 12, at block 310 the method 600 includes inserting the second coherent light 426 into the second waveguide 428 such that the second coherent light 426 exits the second waveguide 428 at the second end 430 of the second waveguide 428 that is embedded within the material 102, thereby causing the second coherent light 426 to interact with the material 102. The second coherent light 426 has the second oscillation frequency $f_2$ that is unequal to the first oscillation frequency $f_1$. At block 312, the method 600 includes detecting the second reaction of the material 102 to the second coherent light 426.

Figure 13:
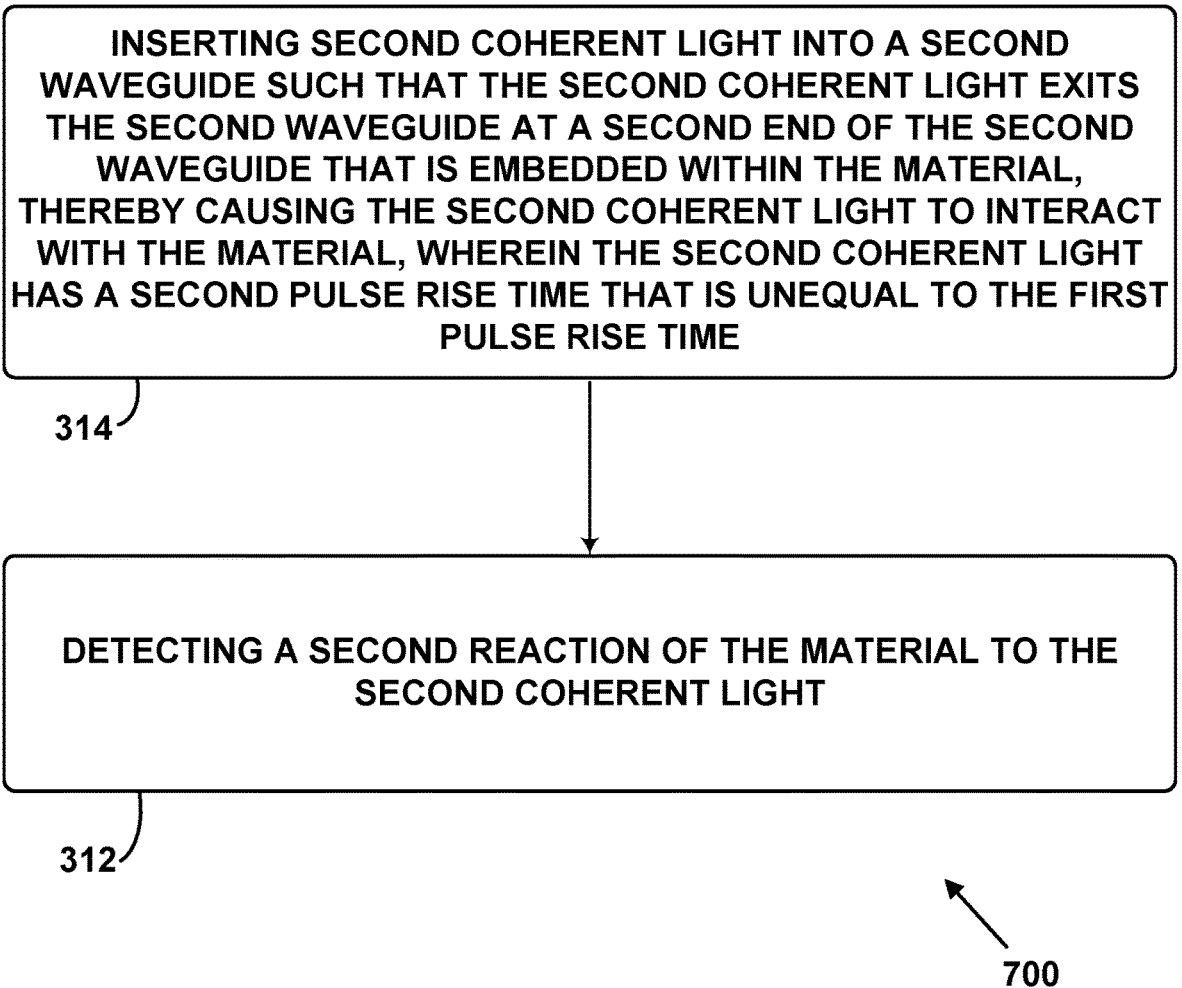
FIG. 13 is a block diagram of a method, according to an example.

In some examples, the coherent light 426 has a first pulse rise time. Referring to FIG. 13, at block 314 the method 700 includes inserting the second coherent light 426 into the second waveguide 428 such that the second coherent light 426 exits the second waveguide 428 at the second end 430 of the second waveguide 428 that is embedded within the material 102, thereby causing the second coherent light 426 to interact with the material 102. The second coherent light 426 has the second pulse rise time that is unequal to the first pulse rise time. At block 312, the method 700 includes detecting the second reaction of the material 102 to the second coherent light 426.

Figure 14:
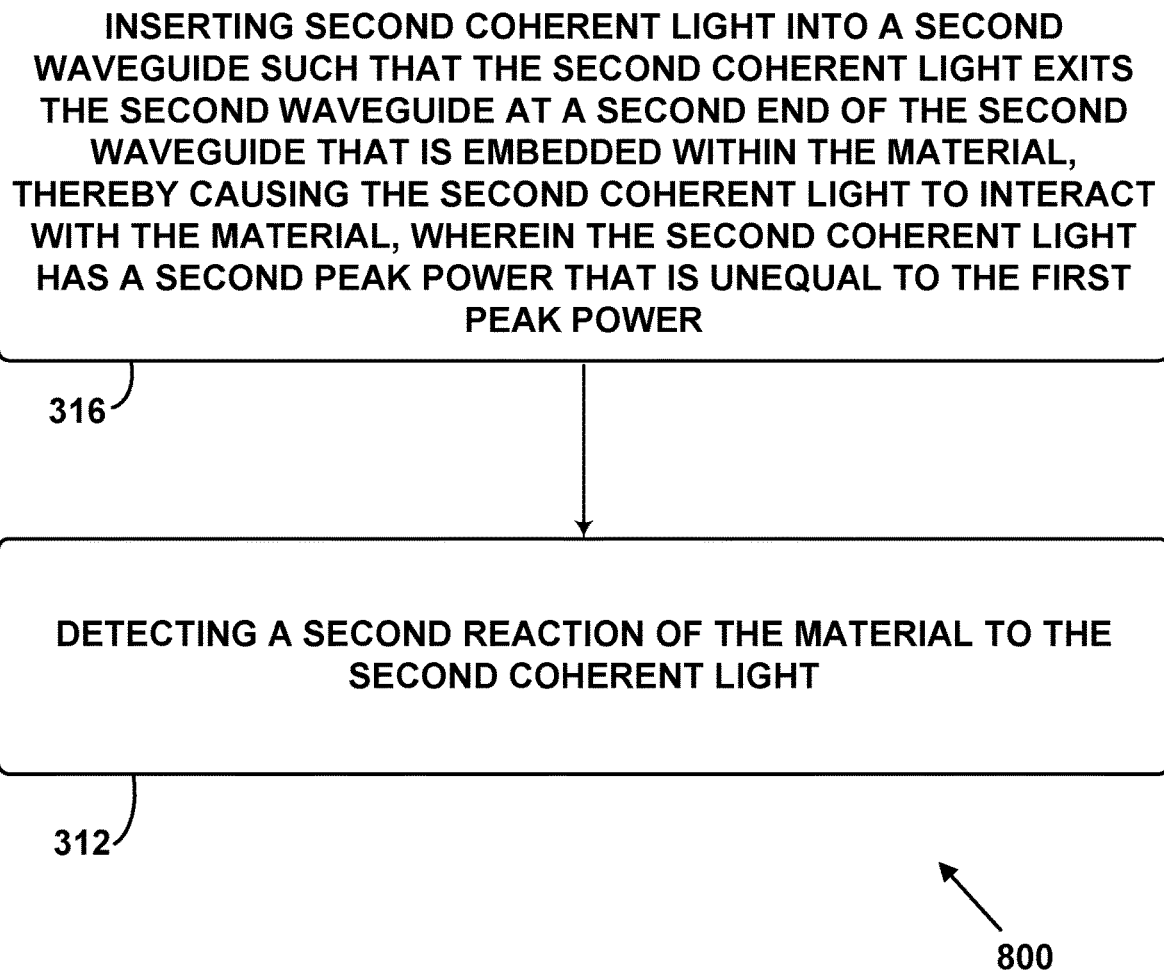
FIG. 14 is a block diagram of a method, according to an example.

In some examples, the coherent light 426 has a first peak power. Referring to FIG. 14, at block 316 the method 800 includes inserting the second coherent light 426 into the second waveguide 428 such that the second coherent light 426 exits the second waveguide 428 at the second end 430 of the second waveguide 428 that is embedded within the material 102, thereby causing the second coherent light 426 to interact with the material 102. The second coherent light 426 has a second peak power that is unequal to the first peak power. At block 312, the method 800 includes detecting the second reaction of the material 102 to the second coherent light 426.

Figure 15:
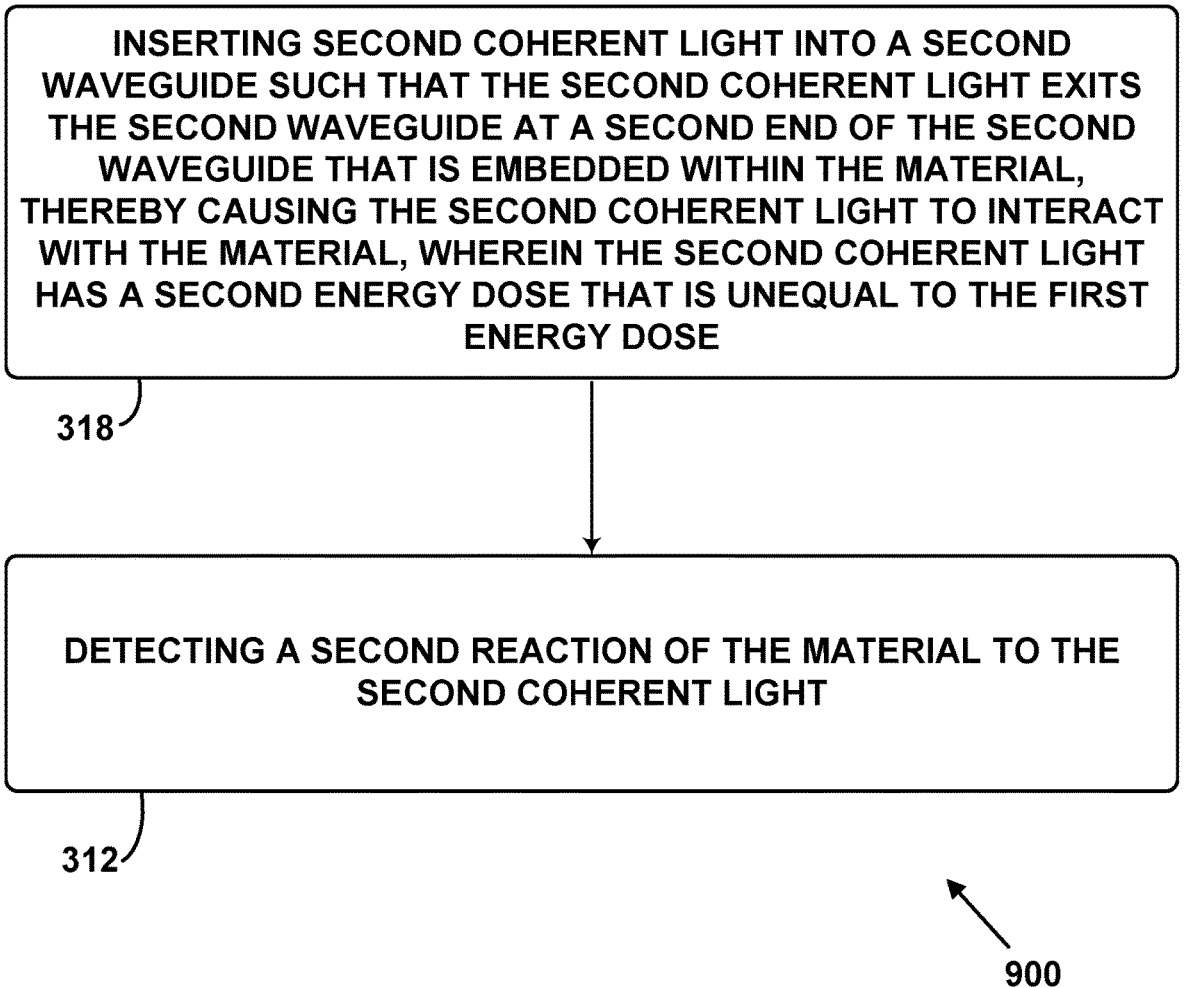
FIG. 15 is a block diagram of a method, according to an example.

In some examples, the coherent light 426 has a first energy dose. Referring to FIG. 15, at block 318 the method 900 includes inserting second coherent light 426 into the second waveguide 428 such that the second coherent light 426 exits the second waveguide 428 at the second end 430 of the second waveguide 428 that is embedded within the material 102, thereby causing the second coherent light 426 to interact with the material 102. The second coherent light 426 has a second energy dose that is unequal to the first energy dose. At block 312, the method 900 includes detecting the second reaction of the material 102 to the second coherent light 426.

In some examples, the coherent light 426 is separated from the edge 408 of the material 102 by the first distance 409. Referring to FIG. 16, at block 320 the method 950 includes inserting the second coherent light 429 into the second waveguide 431 such that the second coherent light 429 exits the second waveguide 431 at the second end 433 of the second waveguide 431 that is embedded within the material 102, thereby causing the second coherent light 429 to interact with the material 102. The second end 433 of the second waveguide 431 is separated from the edge 408 of the material 102 by the second distance 411 that is unequal to the first distance 409. At block 312, the method 950 includes detecting the second reaction of the material 102 to the second coherent light 429.

Examples of the present disclosure can thus relate to one of the enumerated clauses (ECs) listed below.

EC 1 is a method for testing physical properties of a material, the method comprising: inserting coherent light into a waveguide such that the coherent light exits the waveguide at an end of the waveguide that is embedded within the material, thereby causing the coherent light to interact with the material; and detecting a reaction of the material to the coherent light.

EC 2 is the method of EC 1, wherein the waveguide is an optical fiber.

EC 3 is the method of any of ECs 1-2, wherein the waveguide is embedded within a resin layer between a first layer of fibrous material and a second layer of fibrous material, the first layer of fibrous material and the second layer of fibrous material each including fibers embedded within a matrix material.

EC 4 is the method of EC 3, wherein inserting the coherent light comprises inserting the coherent light such that the coherent light impinges the first layer of fibrous material at a first angle, the method further comprising: inserting second coherent light into a second waveguide such that the second coherent light impinges the first layer of fibrous material at a second angle that is unequal to the first angle.

EC 5 is the method of any of ECs 3-4, wherein inserting the coherent light comprises inserting the coherent light such that the coherent light impinges an edge of the material at a first angle, the method further comprising: inserting second coherent light into a second waveguide such that the second coherent light impinges the edge at a second angle that is unequal to the first angle.

EC 6 is the method of any of ECs 1-5, wherein the end of the waveguide is a first end, and wherein inserting the coherent light comprises inserting the coherent light into a second end of the waveguide that is opposite the first end and is outside of the material.

EC 7 is the method of any of ECs 1-6, wherein causing the coherent light to interact with the material comprises causing the coherent light to interact substantially exclusively with a volume of the material that is less than an entirety of the material.

EC 8 is the method of EC 7, wherein causing the coherent light to interact with the material comprises causing adiabatic heating of the volume of the material.

EC 9 is the method of any of ECs 7-8, wherein a transverse cross section of the volume of the material has a first shape that is substantially equivalent to a second shape of the end of the waveguide.

EC 10 is the method of any of ECs 1-9, wherein detecting the reaction comprises detecting light that is emitted from the material.

EC 11 is the method of any of ECs 1-10, wherein detecting the reaction comprises detecting ejection of a particle from the material.

EC 12 is the method of any of ECs 1-11, wherein detecting the reaction comprises detecting a change in physical properties of the material.

EC 13 is the method of any of ECs 1-12, wherein detecting the reaction comprises detecting ejection of gas from the material.

EC 14 is the method of any of ECs 1-13, wherein the coherent light is first coherent light that has a first oscillation frequency, the method further comprising: inserting second coherent light into a second waveguide such that the second coherent light exits the second waveguide at a second end of the second waveguide that is embedded within the material, thereby causing the second coherent light to interact with the material, wherein the second coherent light has a second oscillation frequency that is unequal to the first oscillation frequency; and detecting a second reaction of the material to the second coherent light.

EC 15 is the method of any of ECs 1-14, wherein the coherent light is first coherent light that has a first pulse rise time, the method further comprising: inserting second coherent light into a second waveguide such that the second coherent light exits the second waveguide at a second end of the second waveguide that is embedded within the material, thereby causing the second coherent light to interact with the material, wherein the second coherent light has a second pulse rise time that is unequal to the first pulse rise time; and detecting a second reaction of the material to the second coherent light.

EC 16 is the method of any of ECs 1-15, wherein the coherent light is first coherent light that has a first peak power, the method further comprising: inserting second coherent light into a second waveguide such that the second coherent light exits the second waveguide at a second end of the second waveguide that is embedded within the material, thereby causing the second coherent light to interact with the material, wherein the second coherent light has a second peak power that is unequal to the first peak power; and detecting a second reaction of the material to the second coherent light.

EC 17 is the method of any of ECs 1-16, wherein the coherent light is first coherent light that has a first energy dose, the method further comprising: inserting second coherent light into a second waveguide such that the second coherent light exits the second waveguide at a second end of the second waveguide that is embedded within the material, thereby causing the second coherent light to interact with the material, wherein the second coherent light has a second energy dose that is unequal to the first energy dose; and detecting a second reaction of the material to the second coherent light.

EC 18 is the method of any of ECs 1-17, wherein the end of the waveguide is separated from an edge of the material by a first distance, the method further comprising: inserting second coherent light into a second waveguide such that the second coherent light exits the second waveguide at a second end of the second waveguide that is embedded within the material, thereby causing the second coherent light to interact with the material, wherein the second end of the second waveguide is separated from the edge of the material by a second distance that is unequal to the first distance; and detecting a second reaction of the material to the second coherent light.

EC 19 is a method of forming a test fixture for testing physical properties of a material, the method comprising: forming a first layer of a fibrous material, the fibrous material comprising fibers embedded within a matrix material; forming a second layer of the fibrous material; and forming a resin layer between the first layer and the second layer such that a waveguide is embedded within the resin layer.

EC 20 is a test fixture for testing physical properties of a material, the test fixture comprising: a first layer of a fibrous material, the fibrous material comprising fibers embedded within a matrix material; a second layer of the fibrous material; a resin layer between the first layer of the fibrous material and the second layer of the fibrous material; and a waveguide embedded within the resin layer.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to explain the principles of the examples, the practical application, and to enable others of ordinary skill in the art to understand the disclosure for various examples with various modifications as are suited to the particular use contemplated.

What is claimed is:

1. A method for testing physical properties of a material, the method comprising:
   inserting coherent light into a waveguide such that the coherent light exits the waveguide at an end of the waveguide that is embedded within the material, thereby causing the coherent light to interact with the material after the coherent light exits the waveguide at the end of the waveguide; and
   detecting a reaction of the material to the coherent light that exits the waveguide at the end of the waveguide.

2. The method of claim 1, wherein the waveguide is an optical fiber.

3. The method of claim 1, wherein the waveguide is embedded within a resin layer between a first layer of fibrous material and a second layer of fibrous material, the first layer of fibrous material and the second layer of fibrous material each including fibers embedded within a matrix material.

4. The method of claim 3,
   wherein inserting the coherent light comprises inserting the coherent light such that the coherent light impinges the first layer of fibrous material at a first angle, the method further comprising:
   inserting second coherent light into a second waveguide such that the second coherent light impinges the first layer of fibrous material at a second angle that is unequal to the first angle.

5. The method of claim 3,
   wherein inserting the coherent light comprises inserting the coherent light such that the coherent light impinges an edge of the material at a first angle, the method further comprising:
   inserting second coherent light into a second waveguide such that the second coherent light impinges the edge at a second angle that is unequal to the first angle.

6. The method of claim 1, wherein the end of the waveguide is a first end, and wherein inserting the coherent light comprises inserting the coherent light into a second end of the waveguide that is opposite the first end and is outside of the material.

7. The method of claim 1, wherein causing the coherent light to interact with the material comprises causing the coherent light to interact substantially exclusively with a volume of the material that is less than an entirety of the material.

8. The method of claim 7, wherein causing the coherent light to interact with the material comprises causing adiabatic heating of the volume of the material.

9. The method of claim 7, wherein a transverse cross section of the volume of the material has a first shape that is substantially equivalent to a second shape of the end of the waveguide.

10. The method of claim 1, wherein detecting the reaction comprises detecting light that is emitted from the material.

11. The method of claim 1, wherein detecting the reaction comprises detecting ejection of a particle from the material.

12. The method of claim 1, wherein detecting the reaction comprises detecting a change in physical properties of the material.

13. The method of claim 1, wherein detecting the reaction comprises detecting ejection of gas from the material.

14. The method of claim 1, wherein the coherent light is first coherent light that has a first oscillation frequency, the method further comprising:
   inserting second coherent light into a second waveguide such that the second coherent light exits the second waveguide at a second end of the second waveguide that is embedded within the material, thereby causing the second coherent light to interact with the material, wherein the second coherent light has a second oscillation frequency that is unequal to the first oscillation frequency; and
   detecting a second reaction of the material to the second coherent light.

15. The method of claim 1, wherein the coherent light is first coherent light that has a first pulse rise time, the method further comprising:
   inserting second coherent light into a second waveguide such that the second coherent light exits the second waveguide at a second end of the second waveguide that is embedded within the material, thereby causing the second coherent light to interact with the material, wherein the second coherent light has a second pulse rise time that is unequal to the first pulse rise time; and
   detecting a second reaction of the material to the second coherent light.

16. The method of claim 1, wherein the coherent light is first coherent light that has a first peak power, the method further comprising:
   inserting second coherent light into a second waveguide such that the second coherent light exits the second waveguide at a second end of the second waveguide that is embedded within the material, thereby causing the second coherent light to interact with the material, wherein the second coherent light has a second peak power that is unequal to the first peak power; and
   detecting a second reaction of the material to the second coherent light.

17. The method of claim 1, wherein the coherent light is first coherent light that has a first energy dose, the method further comprising:
   inserting second coherent light into a second waveguide such that the second coherent light exits the second waveguide at a second end of the second waveguide that is embedded within the material, thereby causing the second coherent light to interact with the material, wherein the second coherent light has a second energy dose that is unequal to the first energy dose; and
   detecting a second reaction of the material to the second coherent light.

18. The method of claim 1, wherein the end of the waveguide is separated from an edge of the material by a first distance, the method further comprising:
   inserting second coherent light into a second waveguide such that the second coherent light exits the second waveguide at a second end of the second waveguide that is embedded within the material, thereby causing the second coherent light to interact with the material, wherein the second end of the second waveguide is separated from the edge of the material by a second distance that is unequal to the first distance; and
   detecting a second reaction of the material to the second coherent light.

19. The method of claim 1, wherein the end of the waveguide is completely surrounded by the material.

20. The method of claim 1, wherein the end of the waveguide is separated from any edge of the material.

* * * * *